United States Patent
Haubold et al.

(10) Patent No.: US 9,383,302 B2
(45) Date of Patent: Jul. 5, 2016

(54) METHOD FOR DETERMINING A MACHINING RESULT DURING SURFACE MACHINING OF COMPONENTS

(71) Applicant: Rolls-Royce Deutschland Ltd & Co KG, Blankenfelde-Mahlow (DE)

(72) Inventors: Thomas Haubold, Wehrheim (DE); Wolfgang Hennig, Durham (GB); Goetz Feldmann, Oberursel (DE)

(73) Assignee: Rolls-Royce Deutschland Ltd & Co KG (DE)

( * ) Notice: Subject to any disclaimer, the term of this patent is extended or adjusted under 35 U.S.C. 154(b) by 0 days.

(21) Appl. No.: 14/355,168

(22) PCT Filed: Oct. 31, 2012

(86) PCT No.: PCT/DE2012/001055
§ 371 (c)(1),
(2) Date: Apr. 29, 2014

(87) PCT Pub. No.: WO2013/064139
PCT Pub. Date: May 10, 2013

(65) Prior Publication Data
US 2014/0352450 A1  Dec. 4, 2014

(30) Foreign Application Priority Data

Oct. 31, 2011  (DE) .......................... 10 2011 117 401

(51) Int. Cl.
*G01L 1/24* (2006.01)
*G01N 3/06* (2006.01)
(Continued)

(52) U.S. Cl.
CPC ................ *G01N 3/068* (2013.01); *G01B 11/16* (2013.01); *G01B 11/18* (2013.01); *G01L 1/24* (2013.01); *G01N 21/25* (2013.01); *G01N 2203/0629* (2013.01); *G01N 2203/0652* (2013.01)

(58) Field of Classification Search
CPC ........ G01L 1/24; G01L 5/0052; G01N 21/25; G01N 2203/0629; G01N 3/068; G01N 27/90; C21D 10/00; C21D 10/005
USPC .......................... 73/760, 800, 862.624, 11.02
See application file for complete search history.

(56) References Cited

U.S. PATENT DOCUMENTS 3,950,642 A    4/1976  Feld
4,015,465 A *  4/1977  Scott .............................. 73/800
(Continued)

FOREIGN PATENT DOCUMENTS

DE    2242201       3/1974
DE    2605988 A1   12/1976
(Continued)

OTHER PUBLICATIONS

International Search Report dated Feb. 20, 2013 from counterpart App No. PCT/DE2012/001055.
(Continued)

*Primary Examiner* — Max Noori
(74) *Attorney, Agent, or Firm* — Timothy J. Klima; Shuttleworth & Ingersoll, PLC

(57) ABSTRACT

A method for determining a machining result during surface machining of components, has the following method steps of: providing a component, applying at least one device, which changes under pressure, to the component, machining the surface of the component provided with the at least one device, evaluating the machining operation on the basis of the change in the at least one device as a result of the surface machining of the component. At least one device is in the form of a film which changes at least one property during the surface machining of the component.

12 Claims, 1 Drawing Sheet

(51) Int. Cl.
    *G01B 11/16*     (2006.01)
    *G01N 21/25*     (2006.01)

(56) References Cited

U.S. PATENT DOCUMENTS

| 7,247,074 | B2 * | 7/2007 | Kato et al. ............... 445/24 |
| 8,709,592 | B2 * | 4/2014 | Bird ............... 428/333 |
| 8,720,278 | B1 * | 5/2014 | Toivola et al. ............... 73/762 |
| 2005/0230010 | A1 * | 10/2005 | Tominaga ............ C21D 10/005 148/508 |
| 2011/0182499 | A1 | 7/2011 | Feldmann et al. |
| 2013/0276931 | A1 * | 10/2013 | Fernando et al. ............ 138/137 |

FOREIGN PATENT DOCUMENTS

| DE | 10 2010 001 286 | 7/2011 |
| FR | 2666895 | 3/1992 |
| WO | 01/92843 | 12/2001 |
| WO | 2008/061337 | 5/2008 |

OTHER PUBLICATIONS

German Search Report dated Oct. 5, 2012 from counterpart German App No. 10 2011 117 401.3.

* cited by examiner

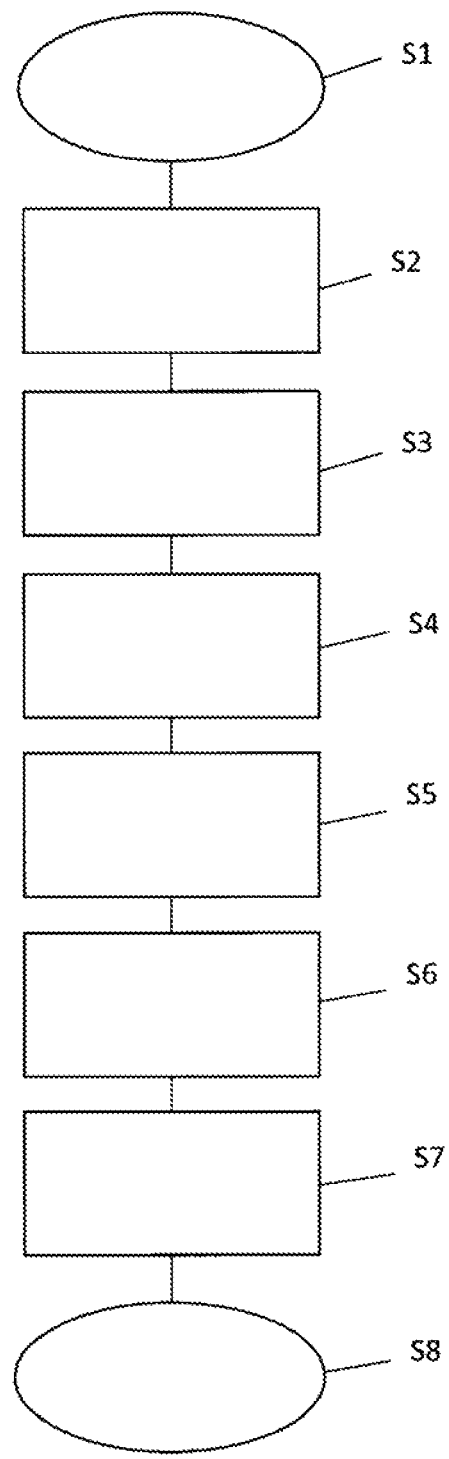

METHOD FOR DETERMINING A MACHINING RESULT DURING SURFACE MACHINING OF COMPONENTS

This application is the National Phase of International Application PCT/DE2012/001055 filed Oct. 31, 2012 which designated the U.S.

This application claims priority to German Patent Application No. DE102011117401.3 filed Oct. 31, 2011, which application is incorporated by reference herein.

This invention relates to a method for determining a treatment result during a surface treatment of components in accordance with the type defined in more detail in present description.

In order to modify a surface or surface layer of components with regard to their properties and to introduce residual stresses, for example, into the component, a number of methods are known, such as shot-peening, rolling, peening, cavitation hardening, laser shock hardening, ultrasonic shot-peening and the like. A measure of this type can for example increase the fatigue strength of components or reduce their susceptibility for crack formation and crack propagation.

To achieve the desired material properties, it is important, for example during rolling, to know as precisely as possible a degree of overlapping of adjacently extending webs of rolling elements. In shot-peening, the corresponding key value is the degree of coverage, which indicates the percentage of the surface of the component impacted by abrasive material, in particular shot.

To achieve a desired degree of coverage in a component, one area of this component is initially peened with a brief exposure time and another unpeened area of this component is then peened with abrasive material for a longer exposure time. After determination of the degree of coverage of the respective component, it is possible with the aid of a stochastic function to calculate what exposure time is needed to set a required degree of coverage, for example 100%. Whether this degree is achieved with the calculated parameters is again determined, with the determination of the parameters being recommended if there is a discrepancy of the calculated results from the measured result.

The degree of coverage is determined visually, for example, in known methods. To do so, the peened component is scrutinized and the degree of coverage is assessed, for example using a magnifying glass. This method is disadvantageously very error-prone, since assessment is made subjectively in each case and the results can fluctuate even with great experience, and can only be determined very roughly.

The visual assessment of the degree of coverage is made more difficult by the fact that assessment of the degree of coverage is dependent on process parameters such as workpiece hardness, abrasive material hardness, abrasive material size, impact angle of the abrasive material jet onto the workpiece surface, peening pressure etc. The surface is harder to assess for smaller abrasive material than for larger abrasive material. A further hindrance to determination of the degree of coverage is caused by non-uniform machining states of the considered component, which can for example be turned, milled, ground or etched.

The coverage can be evaluated using comparative images. During the treatment of components made of different materials, for example titanium, materials on a nickel basis and steel, with different peening parameters, for example abrasive material size, abrasive material velocity and impact angle, different surfaces are created which cannot be evaluated free of errors with a single series of comparative images. The results are also bad to be reproduced and hard to be documented.

The visual method furthermore has the disadvantage that only degrees of coverage of up to 100% can be determined. Degrees of coverage greater than 100% at places on the component hit several times by abrasive material cannot be detected. This may lead to components with low ductility becoming brittle due to excessive peening and being subjected to an increased risk of crack formation or crack propagation.

The impact image can also be assessed with software assistance, for example by grey scale analysis, where a surface image of the treated surface is recorded and, depending on the respective reflection values, it is determined whether the respective area has been impacted or not. Camera systems used here to record the surface image must be calibrated in a time-consuming manner for each individual case.

To facilitate determination of the degree of coverage, the so-called peen scan method is known, where the surface of the component to be peened is provided before peening with a fluorescent paint forming a thin coating. Peening of the component with the abrasive material causes the paint coating to break up and disengage from the component when a certain pressure in the impacted areas is exceeded. To determine the degree of coverage, an assessment is made of the still fluorescent proportion of the surface of the component to the no longer fluorescent proportion of the surface of the component. Differentiating impacted and non-impacted areas can be achieved more easily and reliably. Additionally, computer-assisted determination of the degree of coverage with digitized surface image and subsequent software-assisted evaluation is less error-prone when compared to a method without a coating.

It is a disadvantage for complex components in particular that it is difficult to apply the paint coating evenly, so that there may be areas which had no paint coating even before peening. This is possible in particular in the area of deep grooves, where the paint cannot settle so easily. This falsifies the determination of the degree of coverage, since the areas not covered by the paint coating are regarded during evaluation as peened areas even if they have not been impacted.

Since the paint coating must be applied directly to the component using a suitable device, application in the case of complex components with poorly accessible areas can only be achieved with difficulty or not at all.

The object underlying the present invention is therefore to provide a method for determining a treatment result during a surface treatment of components, by means of which a key value characterizing a treatment state of a component can be precisely determined.

It is a particular object of the present invention to provide solution to the above problems by a method having features as described herein.

The present invention therefore proposes a method for determining a treatment result during a surface treatment of components, said method having the process steps of providing a component, applying at least one device, which changes under pressure, to the component, treating the surface of the component provided with the at least one device, and evaluating the treatment operation on the basis of the change in the at least one device as a result of the surface treatment of the component. In accordance with the invention, it is proposed that at least one device is designed as a film which changes at least one property during the surface treatment of the component.

The key value characterizing the treatment state of the component can be very precisely determined using the method in accordance with the invention, since the film has in all areas a constant thickness and can easily be arranged at poorly accessible places even in the case of complex components. A method in accordance with the invention also has the advantage that the treatment process can easily be evaluated from the change in the property intrinsic to the film. To do so, the film can be evaluated as a whole, so that a detailed place-related assessment of the treatment state is possible.

The film can be attached to various materials with differing treatment states even in poorly accessible areas, with the evaluation of the film being regardless of material properties and treatment states of the component. With the method in accordance with the invention, areas of complex components can be analysed which were not analysable by known methods due to their poor accessibility.

The more precise determination of the result of the treatment process saves time and costs and avoids any repetition of tests. It is also crucial for safety-relevant components, for example blisk blades of jet engines, to treat the surface within close tolerances. Treatment for too long can make the component brittle, so that the surface of the component has a greater tendency to crack formation and propagation. By contrast, too short a treatment can lead to an insufficient strength. With the method in accordance with the invention, a very uniform treatment of the component is possible due to precise adjustability of the treatment parameters, i.e. it can be avoided that some areas are treated too long and other areas too briefly. A fatigue strength of components can thus be optimized.

The film needed for implementation of the method in accordance with the invention is designed and prefabricated in the manner of a blueprint and is hence inexpensive to use. The film provides high reproducibility, and the result of the determination can be documented in simple manner.

The surface of the component can be treated by means of a variety of methods with application of deformation energy. Shot-peening, ultrasonic shot-peening or so-called flapper peening can be used in particular. A degree of coverage for the surface of the component can be determined very precisely here, so that areas with too high a coverage compared with the required coverage can be subjected to less peening. This permits savings in time and costs and prevents the surface or surface layer of the component from becoming brittle, which can be caused by peening an area of the surface with too high a coverage. This in turn has an advantage in respect of the fatigue strength of the treated component. Areas with too low a coverage can also be detected and the peening process adjusted accordingly. Furthermore, safety is increased for components made of materials having a specific maximum coverage beyond which they become brittle.

The surface treatment in a method in accordance with the invention can, alternatively to this, also be achieved for example by means of rolling, laser shock hardening, cavitation hardening, peening, as for example piezo-peening or the like. The method in accordance with the invention is thus usable for a variety of treatment processes with a very wide range of applications to assess a preceding treatment process.

In an advantageous development of a method in accordance with the invention, the at least one film alters its optical state, preferably its colouration, during surface treatment of the component under the effect of deformation energy, in particular under the effect of pressure, with said optical alteration of the film being used to determine the treatment state of the surface of the component. Unlike known methods, in which the component surface is directly evaluated, no three-dimensional surfaces have to be evaluated with the method in accordance with the invention. The evaluation is correspondingly easy to conduct. It is also understood as an optical alteration of the state or a colour change, respectively, when the film for example takes on, from a milky or transparent initial state, one or more shades under the effect of pressure during surface treatment of the component.

If the optical state of the at least one film changes in different degrees depending on the applied deformation energy or on the applied pressure, a deformation energy applied during the treatment process can be determined per surface area. The film can for example be designed pressure-sensitive in a way that it changes its colour in a required pressure range. The film can also be designed such that it takes on differing colour intensities or differing colours in differing pressure ranges.

A simple attachment of the film to the component to be treated is possible when the at least one film has a side adhesive at least in some areas by means of which the film is arranged on the component.

With a strip-shaped design of the film, it can be attached to the component with particular ease. The strips can have here a constant width, so that evaluation of the strips is particularly easy.

In order to permit multiple impacts of abrasive material on an area of the component to be ascertained too, several films overlapping at least in some areas can be arranged on the component.

If several films are arranged on the component, which change their properties in different degrees with the same deformation energy, the treatment state of the component can be analysed with particular precision. The films can in particular have different pressure sensitivities, where a film located closer to the component changes its property especially only with a greater pressure effect occurring during surface treatment, in particular taking on a colour. As a result, degrees of coverage greater than 100% can also be ascertained, so that with rotationally symmetrical components, for example, a spiral generated due to an "incorrect" selection of peening parameters can be determined and the resultant multiple peening of individual areas can be ascertained. It can also be provided that differing films arranged on the component to be treated take on different colours under the effect of pressure.

Particularly easy and quick evaluation of the component treatment process is possible when the at least one film is evaluated in its position attached to the component.

Alternatively, the at least one film can be separated from the component for evaluation. This has the advantage that the film can be evaluated at any location and as a result the analysis of the treatment process at poorly accessible points is made possible in the first place.

The at least one film can be visually evaluated in a simple manner, with this evaluation being made easier compared to known methods in that the treated areas can be made visible with particular clarity.

Alternatively or additionally to the visual evaluation, the at least one film can be initially digitized for evaluation and then evaluated with computer assistance, for example by means of a grey scale analysis.

The features stated herein are suitable, singly or in any combination with one another, for developing the subject matter in accordance with the invention. The respective feature combinations do not represent, with regard to the development of the subject matter according to the invention, any restriction, but have substantially only the character of examples.

Further advantages and advantageous embodiments of the method in accordance with present invention become apparent from the present description and the exemplary embodiment described in principle in the following with reference to the drawing.

The sole FIGURE of the drawing shows a flow chart of a simplified method in accordance with the present invention for determining a treatment result during a surface treatment of components.

The method in accordance with the invention is initiated by the start block S1. A component to be treated is provided in a step S2, where at least one pressure-sensitive film is attached to a component area to be treated in a subsequent step S3. The film has in its basic state a substantially transparent colour, where a colour medium, not appearing coloured, and for example in the form of small balls, is arranged on one side of the film. The film is designed in strip form with one adhesive side and is in the present case arranged adjacently on the component in non-overlapping webs, so that the film is arranged in flat contact and with a constant thickness on the component.

At least one area of the surface of the component on which the films are arranged is treated in the next process step S4 using a shot-peening method. In areas of the component impacted by the abrasive material, the small balls of the film burst, with the paint contained in these balls colouring a further layer of the film through a diaphragm and so marking those areas of the film that were impacted by the abrasive material. In the areas impacted by the abrasive material, the film colours here depending on the level of pressure acting on the respective area—pale red for low pressures or deep red for high pressures.

To determine a degree of coverage in the area treated using the shot-peening method and provided with the film, the film strips are separated from the component in a step S5 and recorded in a digitization step S6 using a camera. Finally, the digital image is analysed and evaluated in an evaluation step S7 using a software. The process sequence then ends with step S8.

It can also be provided that in a first process sequence, the component is peened with a short exposure time and a degree of coverage is determined, and then in a further process sequence an identical component is peened with a longer exposure time. Using mathematical methods, peening parameters which must be set to achieve a required degree of coverage during peening of a component can be determined from the degrees of coverage ascertained for short and long exposure times.

Using the evaluation method, it is possible by analysing the colouration of the individual areas of the film to ascertain which areas of the component were impacted more than once and hence have a degree of coverage greater than 100%. As a result, it can be assured by simple means that the treated component has been produced with a required degree of coverage.

What is claimed is:

1. A method for determining a treatment result during a surface treatment of components, comprising:
   providing a component having a surface,
   applying at least one device, which changes under pressure, to the surface of the component,
   surface treating the surface of the component provided with the at least one device to change the at least one device,
   performing the surface treating by application of deformation energy to the component through the at least one device by at least one chosen from shot-peening, rolling, cavitation hardening and peening, thereby introducing residual stresses into the component, and
   evaluating the surface treating on a basis of the change in the at least one device as a result of the surface treating,
   wherein the at least one device is at least one film which changes at least one property during the surface treating,
   wherein the application of deformation energy is performed to alter a color of the at least one film.

2. The method in accordance with claim 1, and further comprising providing that the film includes a plurality of colorant filled capsules and wherein, application of the deformation energy to the film causes the capsules to burst and color the film.

3. The method in accordance with claim 1, wherein the at least one film is digitized for evaluation and then evaluated with computer assistance.

4. The method in accordance with claim 1, wherein the color of the at least one film changes in different degrees depending on a degree of the deformation energy applied.

5. The method in accordance with claim 1, wherein the at least one film has a side adhesive at least in some areas by which the at least one film is applied to the component.

6. The method in accordance with claim 1, wherein the at least one film is arranged in strips on the component.

7. The method in accordance with claim 1, wherein a plurality of films overlapping at least in some areas are arranged on the component.

8. The method in accordance with claim 1, wherein a plurality of films are arranged on the component, with properties of the plurality of films changing in different degrees with a same amount of the deformation energy.

9. The method in accordance with claim 1, wherein the at least one film is evaluated while attached to the component.

10. The method in accordance with claim 1, wherein the at least one film is separated from the component for evaluation.

11. The method in accordance with claim 1, wherein the at least one film is visually evaluated.

12. The method in accordance with claim 4, and further comprising providing that the film includes a plurality of colorant filled capsules and wherein, application of the deformation energy to the film causes the capsules to burst and color the film.

* * * * *